(12) United States Patent
Koyrakh et al.

(10) Patent No.: US 7,062,315 B2
(45) Date of Patent: Jun. 13, 2006

(54) AUTOMATED TEMPLATE GENERATION ALGORITHM FOR IMPLANTABLE DEVICE

(75) Inventors: Lev A. Koyrakh, Plymouth, MN (US); Eugene Davydov, Stanford, CA (US); Jeffrey M. Gillberg, Coon Rapids, MN (US); Jian Cao, Maplewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 620 days.

(21) Appl. No.: 10/132,773

(22) Filed: Apr. 25, 2002

(65) Prior Publication Data

US 2002/0193695 A1 Dec. 19, 2002

Related U.S. Application Data

(60) Provisional application No. 60/286,467, filed on Apr. 25, 2001, provisional application No. 60/253,555, filed on Nov. 28, 2000.

(51) Int. Cl.
*A61B 5/04* (2006.01)

(52) U.S. Cl. .................................. 600/515; 600/518

(58) Field of Classification Search ................ 600/515, 600/521, 518; 607/4, 5, 14
See application file for complete search history.

(56) References Cited

U.S. PATENT DOCUMENTS

| | | | |
|---|---|---|---|
| 4,375,817 A | 3/1983 | Engle et al. | 128/419 D |
| 4,384,585 A | 5/1983 | Zipes | 128/419 D |
| 4,548,209 A | 10/1985 | Wielders et al. | 128/419 D |
| 4,577,633 A | 3/1986 | Berkovits et al. | 128/419 PG |
| 4,587,970 A | 5/1986 | Holley et al. | 128/419 D |
| 4,693,253 A | 9/1987 | Adams | 128/419 D |
| 4,726,380 A | 2/1988 | Vollmann et al. | 128/419 PG |
| 4,727,380 A | 2/1988 | Miura et al. | 346/108 |
| 4,800,883 A | 1/1989 | Winstrom | 128/419 D |
| 4,819,643 A | 4/1989 | Menken | 128/419 P |
| 4,830,006 A | 5/1989 | Haluska et al. | 128/419 PG |
| 4,880,004 A | 11/1989 | Baker, Jr. et al. | 128/419 PG |
| 4,880,005 A | 11/1989 | Pless et al. | 128/419 PG |
| 4,949,719 A | 8/1990 | Pless et al. | 128/419 D |
| 4,949,730 A | 8/1990 | Cobben et al. | 128/775 |
| 4,953,551 A | 9/1990 | Mehra et al. | 128/419 D |
| 5,117,824 A | 6/1992 | Keimel et al. | 128/419 D |
| 5,163,427 A | 11/1992 | Keimel | 128/419 D |

(Continued)

FOREIGN PATENT DOCUMENTS

EP 0 506 230 A1 9/1992

(Continued)

OTHER PUBLICATIONS

U.S. Appl. No. 09/995,176, filed Nov. 26, 2001, entitled "Automated Template Generation Algorithm for Implantable Device".

(Continued)

*Primary Examiner*—George R. Evanisko
*Assistant Examiner*—Michael Kahelin
(74) *Attorney, Agent, or Firm*—Michael C. Soldner; Girma Wolde-Michael

(57) ABSTRACT

A method of generating a template in an implantable medical device for implantation within a patient, and a processor readable medium for performing the method, that includes generating a template from collected events corresponding to the patient, delaying the generation of the template for a first predetermined time period in response to the template not being generated within a predetermined number of collected events, determining whether the template is valid, and monitoring the template to determine whether the template is an accurate representation of the patient.

21 Claims, 9 Drawing Sheets

U.S. PATENT DOCUMENTS

| | | | | |
|---|---|---|---|---|
| 5,188,105 A | 2/1993 | Keimel | ............. | 128/419 D |
| 6,312,388 B1 * | 11/2001 | Marcovecchio et al. | .... | 600/508 |
| 6,393,316 B1 | 5/2002 | Gillberg et al. | ............. | 600/515 |
| 6,409,776 B1 | 6/2002 | Yan et al. | ............. | 29/25.03 |
| 6,745,068 B1 * | 6/2004 | Koyrakh et al. | ............. | 600/515 |

FOREIGN PATENT DOCUMENTS

| | | |
|---|---|---|
| EP | 0 848 965 A2 | 6/1998 |
| WO | WO 00/47275 | 2/2000 |
| WO | WO 00/53088 | 3/2000 |

OTHER PUBLICATIONS

Olson et al., "Onset and Stability for Ventricular Tachyarrhythmia Detection in an Implantable Pacer-Cardioverter-Defibrillator", *Computers in Cardiology*, Oct. 7-10, 1986, IEEE Computer Society Press, pp. 167-170.

* cited by examiner

AUTOMATED TEMPLATE GENERATION ALGORITHM FOR IMPLANTABLE DEVICE

RELATED APPLICATIONS

This application claims priority to U.S. Provisional Patent Application Ser. No. 60/286,467, filed Apr. 25, 2001, entitled "AUTOMATED TEMPLATE GENERATION ALGORITHM FOR IMPLANTABLE ICD", incorporated herein by reference in its entirety.

Cross-reference is hereby made to U.S. Provisional Patent Application Ser. No. 60/253,555, filed Nov. 28, 2000, entitled "AUTOMATED TEMPLATE GENERATION ALGORITHM FOR IMPLANTABLE ICD", now U.S. application Ser. No. 09/995,176, filed Nov. 26, 2001, entitled "AUTOMATED TEMPLATE GENERATION ALGORITHM FOR IMPLANTABLE DEVICE".

FIELD OF THE INVENTION

The present invention relates generally to a physiological waveform morphology discrimination method for use in an implantable medical device, and in particular, the present invention relates to automatic creation of a template for EGM morphology measurements in an implantable medical device.

BACKGROUND OF THE INVENTION

In the medical fields of cardiology and electrophysiology, many tools are used to assess the condition and function of a patient's heart, including the observed frequency, polarity and amplitudes of the PQRST complex associated with a heart cycle. Such tools include classic external ECG systems for displaying and recording the characteristic lead ECG signals from skin electrodes placed on the patient's chest and limbs, ambulatory ECG Holter monitors for continuously recording the ECG or segments thereof from a more limited set of skin electrodes for a period of time, and more recently developed completely implantable cardiac monitors or cardiac pacemakers and pacemaker/cardioverter/defibrillators (PCDS) or implantable cardioverter/defibrillators (ICDs) having the capability of recording EGM segments or data derived from atrial and ventricular EGMS (A-EGMs and V-EGMs) for telemetry out to an external programmer for external storage and display.

One of the problems addressed in the design of implantable PCDs or ICDs is the avoidance of unnecessary electrical shocks delivered to a patient's heart in response to rapid heart rates caused by exercise (sinus tachycardia) or by atrial fibrillation. Such rhythms are known collectively as supraventricular tachycardias (SVTs). Studies have shown that SVTs may occur in up to 30% of ICD patients. While ICDs are generally effective at identifying ventricular tachycardia events, the ICD can occasionally deliver a therapy to treat what is detected as being a ventricular tachycardia when in fact the source of the event is related to a supraventricular tachycardia event. Since delivery of the treatment is painful and disconcerting to the patient, deficiencies in distinguishing ventricular tachycardia events from supraventricular tachycardia events tends to be problematic, making the reduction of the incidences of inappropriate treatment highly desirable.

One approach to the problem of distinguishing between normal ORS complexes present during SVTs from those indicative of a VT is to study the morphology of the QRS complex and discriminate normal heart beats from abnormal ones based on the similarity of the signal to a sample waveform recorded from the normal heartbeat, typically referred to as a template. Since a normal QRS complex, or slow rate rhythm, is generally narrower than the QRS complex during VT, or fast rate rhythm, one of the existing methods to discriminate between VT and normal EGM waveforms is based on the properly measured width of the QRS complex. By creating the template based on information sensed from supraventricular rhythm complexes, the ICD is able to compare cardiac complexes sensed during tachycardia episodes against the supraventricular rhythm template. Based on the results of the comparison, the ICD is able to classify the tachycardia episodes as being either a VT complex or a SVT complex, and delivers therapy according to the classification.

In theory, the shape of the QRS complex in the EGM signal during SVT will not change significantly in most patients, because ventricular depolarizations are caused by normal HIS-Purkinje conduction from the atrium to the ventricle. If high ventricular rates are due to a ventricular tachycardia (VT), one can expect a very different morphology of the electrogram (EGM) signal of the ventricular depolarization (QRS complex) because of a different pattern of electrical activity of the heart during VT. However, in certain instances, such as during the electrode/tissue maturation process, or when the patient begins taking new or additional medications, develops a myocardial infarction, or experiences other physiological changes causing the electrical tissue of the patient to change, the morphology of the normal heart rhythm of the patient may change from that originally used as a basis for creating the template. As a result, since deviation from the "normal" heart rhythm of the patient occurs, the template begins to become corrupted, no longer being representative of the patient's current normal heart rhythm and therefore causing the number of inappropriately delivered therapies to increase.

In addition to reducing delivery of inappropriate therapy, another major consideration to be taken into account in the development of the ICD is the limited battery power of the ICD that is available. Since the batteries supplied in the ICD cannot be replaced after initial implantation of the device without surgical procedures, the entire ICD must typically be surgically replaced once the batteries become depleted, making it very desirable to conserve battery power of the ICD. As a result, one of the ways to conserve battery power is to reduce the current drain by reducing the complexity of the signal processing that must be performed by the ICD, limiting the available solutions to reduction of inappropriate therapy delivery. Accordingly, what is needed is a method for reducing the instances of inappropriate therapy delivery that maximizes conservation of the battery power of the device.

SUMMARY OF THE INVENTION

The present invention relates to a method of generating a template in an implantable medical device for implantation within a patient, and a processor readable medium for performing the method, that includes generating a template from collected events corresponding to the patient, delaying generation of the template for a first predetermined time period in response to the template not being generated within a predetermined number of collected events, determining whether the template is valid, and monitoring the template to determine whether the template is an accurate representation of the patient.

According to a preferred embodiment of the present invention, the step of generating a template includes monitoring a heart rate of the patient to generate the collected events, determining whether beats corresponding to the collected events are normal beats, and determining whether a predetermined number of normal beats has been collected within the predetermined number of collected events, wherein the step of delaying the template generation includes delaying the template generation in response to the predetermined number of normal beats not being collected within the predetermined number of collected events.

According to another aspect of the present invention, the step of generating a template includes determining whether the predetermined number of normal beats have been collected and computing cross matches between the predetermined number of collected normal beats to form corresponding computed cross matches, determining whether a predetermined number of the computed cross matches exceed a threshold, determining whether a predetermined number of cross matching attempts have failed, delaying the template generation for a second predetermined time period in response to the predetermined number of failed cross matching attempts, and forming the template from the predetermined number of computed cross matches in response to the predetermined number of the computed cross matches exceeding the threshold.

According to yet another aspect of the present invention, the step of determining whether the template is valid includes collecting subsequent normal beats within a second predetermined time period, computing a match between the subsequently collected normal beats and the template, determining whether the match is within a predetermined threshold to form matched beats and other than matched beats, determining whether the other than matched beats is greater than a first number of beats, and determining the template is valid in response to the matched beats being greater than or equal to a second number of beats.

According to still another aspect of the present invention, the step of monitoring the template includes, in response to a predetermined number of subsequent beats being other than matched beats, determining whether an average degree of similarity between the other than matched beats and the template is less than a predetermined threshold, deleting the template in response to the average degree of similarity between the other than matched beats and the template being less than the predetermined threshold, and generating a template in response to the average degree of similarity between the other than matched beats and the template being greater than or equal to the predetermined threshold.

BRIEF DESCRIPTION OF THE DRAWINGS

The features of the present invention which are believed to be novel are set forth with particularity in the appended claims. The invention, together with further objects and advantages thereof, may best be understood by making reference to the following description, taken in conjunction with the accompanying drawings, in the several figures of which like reference numerals identify like elements, and wherein:

DETAILED DESCRIPTION OF THE PREFERRED EMBODIMENTS

Figure 1:
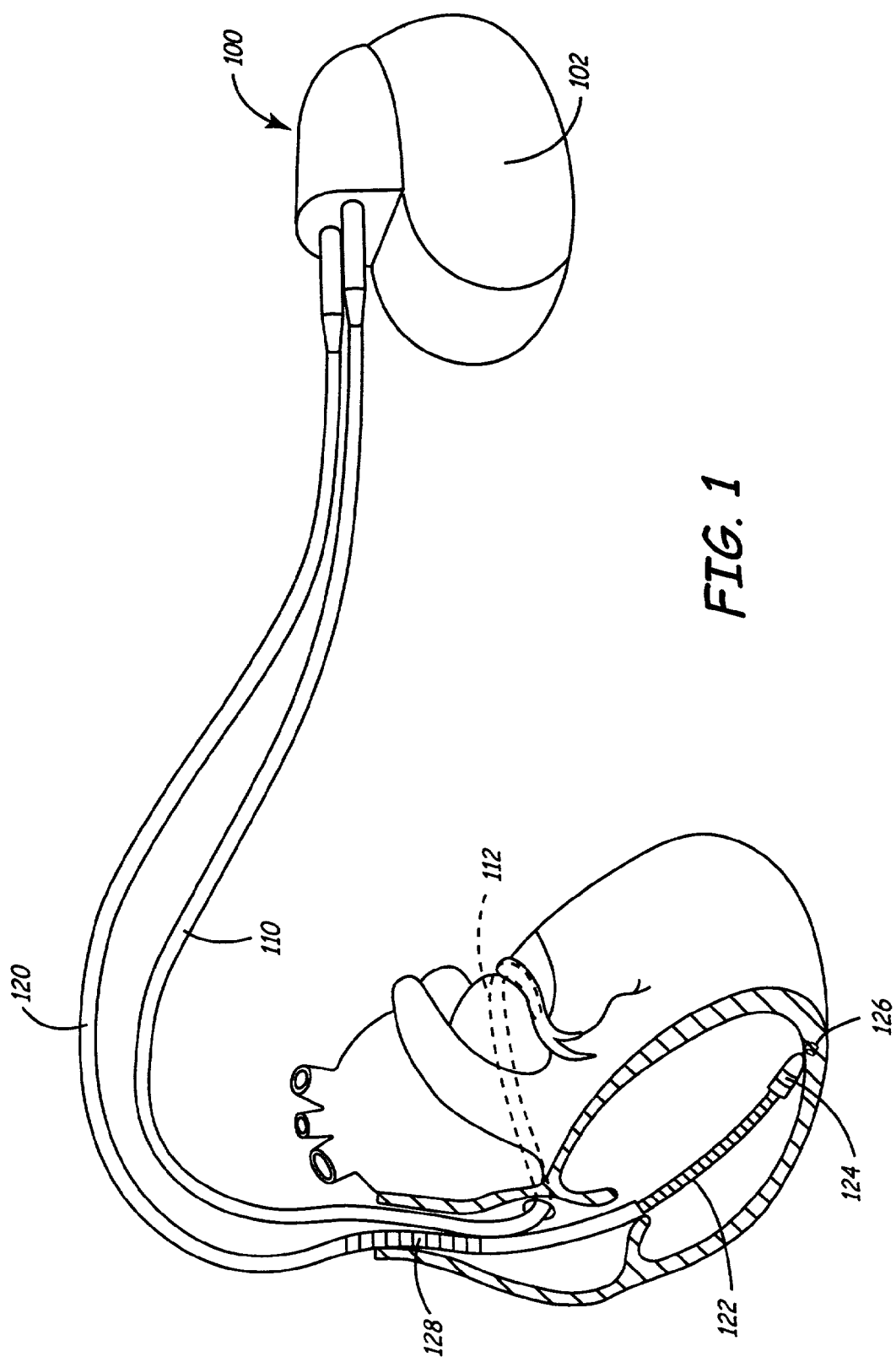
FIG. 1 illustrates an implantable medical device and its associated lead system, as implanted in and adjacent to the heart.

FIG. 1 is a schematic diagram of an implantable medical device for utilizing the template generation according to the present invention. As illustrated in FIG. 1, an implantable medical device 100, such as a pacemaker/cardioverter/defibrillator includes a lead system having a coronary sinus lead 110, a right ventricular lead 120, and a subcutaneous lead (not shown). Coronary sinus lead 110 is provided with an elongated electrode located in the coronary sinus and great vein region at 112, extending around the heart until approximately the point at which the great vein turns downward toward the apex of the heart. Right ventricular lead 120 includes two elongated defibrillation electrodes 122 and 128, a ring electrode 124, and helical electrode 126, which is screwed into the tissue of the right ventricle at the right ventricular apex. A housing 102 of defibrillator 100 may serve as an additional electrode.

In conjunction with the present invention, the lead system illustrated provides electrodes that may be used to detect electrical activity in the ventricles. For example, ring electrode 124 and tip electrode 126 may be used to detect the occurrence of an R-wave and ring electrode 124 and a subcutaneous defibrillation electrode (not shown) may be used to provide an EGM signal stored in response to R-wave detect. Alternatively, electrodes 124 and 126 may be used for both R-wave detection and as a source for the stored digitized EGM signal used for morphology analysis. According to a preferred embodiment of the present invention, electrodes 122 and 102 are utilized for morphology analysis. Other electrode configurations may also be employed. In alternative embodiments in which atrial depolarizations are of interest, sensing electrodes would correspondingly be placed in or adjacent the patients atria.

Figure 2:
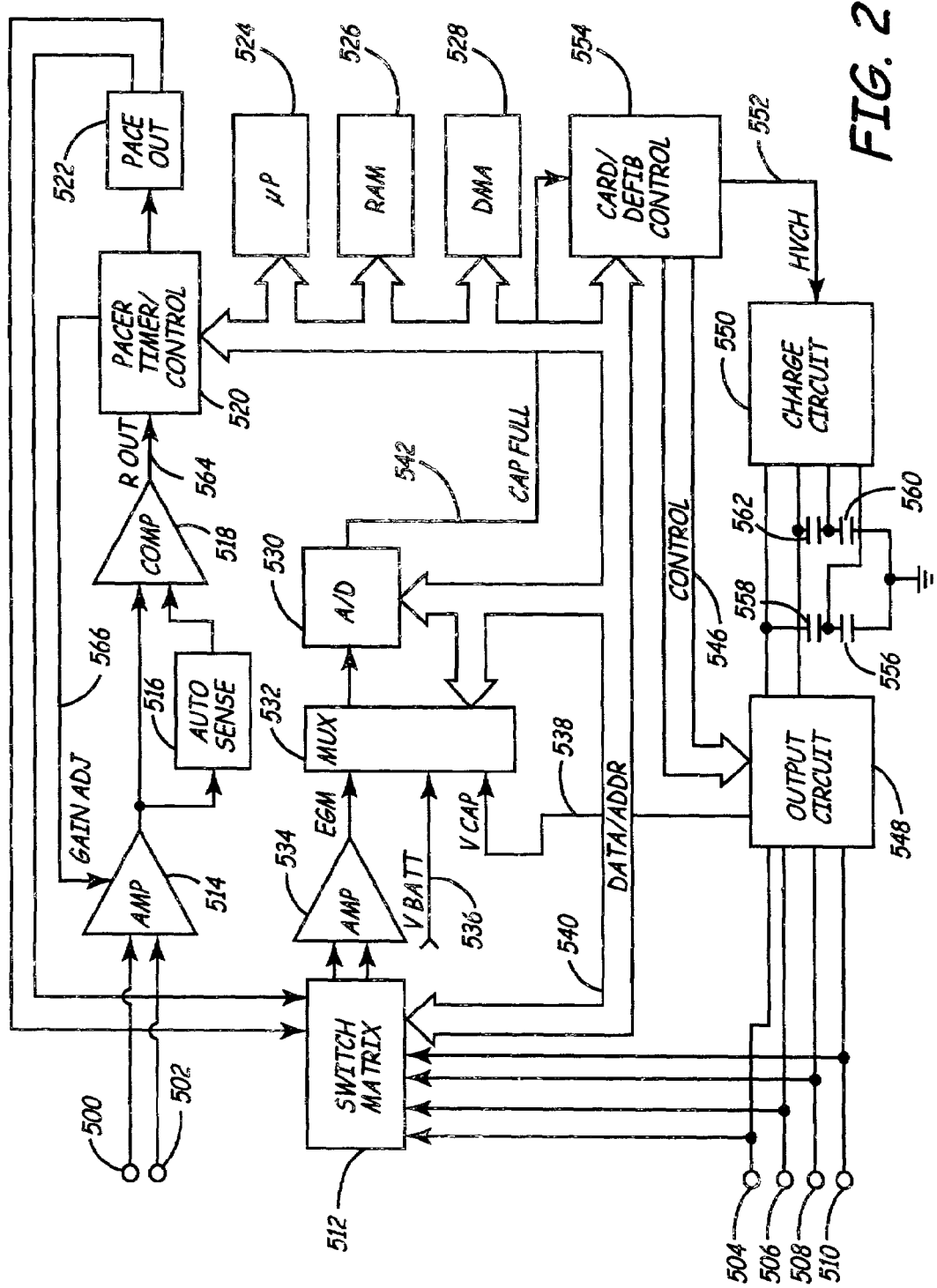
FIG. 2 is a functional schematic diagram of an implantable medical device in which the present invention may usefully be practiced.

FIG. 2 is a functional schematic diagram of an implantable medical device in which the present invention may usefully be practiced. This diagram should be taken as exemplary of the type of device in which the invention may be embodied, and not as limiting, as it is believed that the invention may usefully be practiced in a wide variety of device implementations, including devices having functional organization similar to any of the implantable pacemaker/cardioverter/defibrillators presently being implanted for clinical evaluation in the United States. The invention is also believed practicable in conjunction with implantable pacemaker/cardioverters/defibrillators as disclosed in prior U.S. Pat. No. 4,548,209, issued to Wielders, et al. on Oct. 22, 1985, U.S. Pat. No. 4,693,253, issued to Adams et al. on Sep. 15, 1987, U.S. Pat. No. 4,830,006, issued to Haluska et al. on May 6, 1989 and U.S. Pat. No. 4,949,730, issued to Pless et al. on Aug. 21,1990, all of which are incorporated herein by reference in their entireties.

The device is illustrated as being provided with six electrodes, 500, 502, 504, 506, 508 and 510. Electrodes 500 and 502 may be a pair of electrodes located in the ventricle, for example, corresponding to electrodes 124 and 126 in FIG. 1. Electrode 504 may correspond to a remote, electrode located on the housing of the implantable pacemaker/cardioverter/defibrillator. Electrodes 506, 508 and 510 may correspond to the large surface area defibrillation electrodes located on the ventricular and coronary sinus leads illustrated in FIG. 1 or to epicardial or subcutaneous defibrillation electrodes.

Electrodes 500 and 502 are shown as hard-wired to the R-wave detector circuit which includes a band pass amplifier 514, an auto-threshold circuit 516 for providing an adjustable sensing threshold as a function of the measured R-wave amplitude and a comparator 518. A signal is generated on R-out line 564 whenever the signal sensed between electrodes 500 and 502 exceeds the present sensing threshold defined by auto threshold circuit 516. As illustrated, the gain on the band pass amplifier 514 is also adjustable by means of a signal from the pacer timing/control circuitry 520 on GAIN ADJ line 566.

The operation of this R-wave detection circuitry may correspond to that disclosed in U.S. Pat. No. 5,117,824 by Keimel, et al., issued Jun. 2, 1992, incorporated herein by reference in its entirety. However, alternative R-wave detection circuitry such as that illustrated in U.S. Pat. No. 4,819,643, issued to Menken on Apr. 11, 1989 and U.S. Pat. No. 4,880,004, issued to Baker et al. on Nov. 14, 1989, both incorporated herein by reference in their entireties, may also usefully be employed to practice the present invention.

Threshold adjustment circuit 516 sets a threshold corresponding to a predetermined percentage of the amplitude of a sensed R-wave, with the threshold decaying to a minimum threshold level over a period of less than three seconds thereafter, similar to the automatic sensing threshold circuitry illustrated in the article "Reliable R-Wave Detection from Ambulatory Subjects", by Thakor et al., published in Biomedical Science Instrumentation, Vol. 4, pp 67–72, 1978, incorporated herein by reference in its entirety. An improved version of such an amplifier is disclosed in U.S. patent application Ser. No. 09/250,065, filed Feb. 12, 1999 by Rajasekhar, et al., for an "Implantable Device with Automatic Sensing Adjustment", also incorporated herein by reference in its entirety. The invention may also be practiced in conjunction with more traditional R-wave sensors of the type comprising a band pass amplifier and a comparator circuit to determine when the band-passed signal exceeds a predetermined, fixed sensing threshold.

Switch matrix 512 is used to select which of the available electrodes make up the second electrode pair for use in conjunction with the present invention. The second electrode pair may include electrode 502 or 500 in conjunction with electrode 504, 506, 508 or 510, or may include other combinations of the illustrated electrodes, including combinations of the large surface defibrillation electrodes 506, 508, 510. Selection of which two electrodes are employed as the second electrode pair in conjunction with R-wave width measurement function is controlled by the microprocessor 524 via data/address bus 540. Signals from the selected electrodes are passed through band-pass amplifier 534 and into multiplexer 532, where they are converted to multi-bit digital signals by A/D converter 530, for storage in random access memory 526 under control of direct memory address circuit 528. Microprocessor 524 employs the digitized EGM signal stored in random access memory 526 in conjunction with the morphology analysis method utilized. For example, the microprocessor 524 may analyze the EGM stored in an interval extending from 100 milliseconds previous to the occurrence of an R-wave detect signal on line 564, until 100 milliseconds following the occurrence of the R-wave detect signal. Alternatively, microprocessor may 524 may analyze the width of the patient's R-wave to generate the template, as described, for example, in U.S. Pat. No. 5,312,441, issued to Mader et al. on May 17, 1994, and incorporated herein by reference in it's entirety. The operation of microprocessor 524 in performing the template generation method of the present invention is controlled by means of software stored in ROM, associated with microprocessor 524.

The remainder of the circuitry is dedicated to the provision of cardiac pacing, cardioversion and defibrillation therapies. Pacer timing/control circuitry 520 includes programmable digital counters which control the basic time intervals associated with VVI mode cardiac pacing, including the pacing escape intervals, the refractory periods during which sensed R-waves are ineffective to restart timing of the escape intervals and the pulse width of the pacing pulses. The durations of these intervals are determined by microprocessor 524, and are communicated to pacing circuitry 520 via address/data bus 540. Pacer timing/control circuitry 520 also determines the amplitude of the cardiac pacing pulses and the gain of band-pass amplifier, under control of microprocessor 524.

During VVI mode pacing, the escape interval counter within pacer timing/control circuitry 520 is reset upon sensing of an R-wave as indicated by a signal on line 564, and on timeout triggers generation of a pacing pulse by pacer output circuitry 522, which is coupled to electrodes 500 and 502. The escape interval counter is also reset on generation of a pacing pulse, and thereby controls the basic timing of cardiac pacing functions, including anti-tachycardia pacing. The duration of the interval defined by the escape interval timer is determined by microprocessor 524, via data/address bus 540. The value of the count present in the escape interval counter when reset by sensed R-waves may be used to measure the duration of R—R intervals, to detect the presence of tachycardia and to determine whether the minimum rate criteria are met for activation of the width measurement function.

Microprocessor 524 operates as an interrupt driven device, under control of software stored in the ROM associated with microprocessor 524 and responds to interrupts from pacer timing/control circuitry 520 corresponding to the occurrence of sensed R-waves and corresponding to the generation of cardiac pacing pulses. These interrupts are provided via data/address bus 540. Any necessary mathematical calculations to be performed by microprocessor 524 and any updating of the values or intervals controlled by pacer timing/control circuitry 520 take place following such interrupts. These calculations include those described in more detail below associated with the discrimination methods of the present invention.

In the event that a tachycardia is detected, and an anti-tachycardia pacing regimen is desired, appropriate timing intervals for controlling generation of antitachycardia pacing therapies are loaded from microprocessor 524 into pacer timing/control circuitry 520, to control the operation of the escape interval counter and to define refractory periods during which detection of an R-wave by the R-wave detection circuitry is ineffective to restart the escape interval counter. Similarly, in the event that generation of a cardioversion or defibrillation pulse is required, microprocessor 524 employs the counters to in pacer timing/control circuitry 520 to control timing of such cardioversion and defibrillation pulses, as well as timing of associated refractory periods during which sensed R-waves are ineffective to reset the timing circuitry.

In response to the detection of fibrillation or a tachycardia requiring a cardioversion pulse, microprocessor 524 activates cardioversion/defibrillation control circuitry 554, which initiates charging of the high voltage capacitors 556, 558, 560 and 562 via charging circuit 550, under control of high voltage charging line 552. The voltage on the high voltage capacitors is monitored via VCAP line 538, which is passed through multiplexer 532, and, in response to reaching a predetermined value set by microprocessor 524, results in generation of a logic signal on CAP FULL line 542, terminating charging. Thereafter, delivery of the timing of the defibrillation or cardioversion pulse is controlled by pacer timing/control circuitry 520. One embodiment of an appropriate system for delivery and synchronization of cardioversion and defibrillation pulses, and controlling the timing functions related to them is disclosed in more detail in U.S. Pat. No. 5,188,105, issued to Keimel on Feb. 23, 1993 and incorporated herein by reference in its entirety. However, any known cardioversion or defibrillation pulse generation circuitry is believed usable in conjunction with the present invention. For example, circuitry controlling the timing and generation of cardioversion and defibrillation pulses as disclosed in U.S. Pat. No. 4,384,585, issued to Zipes on May 24, 1983, in U.S. Pat. No. 4,949,719 issued to Pless et al., cited above, and in U.S. Pat. No. 4,375,817, issued to Engle et al., all incorporated herein by reference in their entireties may also be employed. Similarly, known circuitry for controlling the timing and generation of antitachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are incorporated herein by reference in their entireties may also be used.

In modern pacemaker/cardioverter/defibrillators, the particular antitachycardia and defibrillation therapies are programmed into the device ahead of time by the physician, and a menu of therapies is typically provided. For example, on initial detection of tachycardia, an anti-tachycardia pacing therapy may be selected. On redetection of tachycardia, a more aggressive anti-tachycardia pacing therapy may be scheduled. If repeated attempts at anti-tachycardia pacing therapies fail, a higher-level cardioversion pulse therapy may be selected thereafter. Prior art patents illustrating such pre-set therapy menus of anti-tachyarrhythmia therapies include the above-cited U.S. Pat. No. 4,830,006, issued to Haluska, et al., U.S. Pat. No. 4,726,380, issued to Vollmann et al. and U.S. Pat. No. 4,587,970, issued to Holley et al. The present invention is believed practicable in conjunction with any of the known anti-tachycardia pacing and cardioversion therapies, and it is believed most likely that the invention of the present application will be practiced in conjunction with a device in which the choice and order of delivered therapies is programmable by the physician, as in current implantable pacemaker/cardioverter/defibrillators.

In the present invention, selection of the particular electrode configuration for delivery of the cardioversion or defibrillation pulses is controlled via output circuit 548, under control of cardioversion/defibrillation control circuitry 554 via control bus 546. Output circuit 548 determines which of the high voltage electrodes 506, 508 and 510 will be employed in delivering the defibrillation or cardioversion pulse regimen, and may also be used to specify a multielectrode, simultaneous pulse regimen or a multielectrode sequential pulse regimen. Monophasic or biphasic pulses may be generated. One example of circuitry which may be used to perform this function is set forth in U.S. Pat. No. 5,163,427, issued to Keimel on Nov. 17, 1992, incorporated herein by reference in its entirety. However, output control circuitry as disclosed in U.S. Pat. No. 4,953,551, issued to Mehra et al. on Sep. 4, 1990 or U.S. Pat. No. 4,800,883, issued to Winstrom on Jan. 31, 1989 both incorporated herein by reference in their entireties, may also be used in the context of the present invention. Alternatively single monophasic pulse regimens employing only a single electrode pair according to any of the above-cited references that disclose implantable cardioverters or defibrillators may also be used.

As discussed above, switch matrix 512 selects which of the various electrodes are coupled to band pass amplifier 534. Amplifier 534 may be a band-pass amplifier, having a band pass extending for approximately 2.5 to 100 hertz. The filtered EGM signal from amplifier 534 is passed through multiplexer 532, and digitized in A-D converter circuitry 530. The digitized EGM data is stored in random access memory 526 under control of direct memory address circuitry 528. Preferably, a portion of random access memory 526 is configured as a looping or buffer memory, which stores at least the preceding several seconds of the EGM signal.

The occurrence of an R-wave detect signal on line 564 is communicated to microprocessor 524 via data/address bus 540, and microprocessor 524 notes the time of its occurrence. If the morphology analysis function is activated, microprocessor 524 may, for example, wait 100 milliseconds or other physician selected interval following the occurrence of the R-wave detect signal, and thereafter transfer the most recent 200 milliseconds or other physician selected interval of digitized EGM stored in the looping or buffer memory portion of the random access memory circuit 526 to a second memory location, where the contents may be digitally analyzed according to the present invention. In this case, the transferred 200 milliseconds of stored EGM will correspond to a time window extending 100 milliseconds on either side of the R-wave detect signal. Window sizes in any case should be sufficient to allow analysis of the entire QRS complexes associated with the detected R-waves. The microprocessor also updates software-defined counters that hold information regarding the R—R intervals previously sensed. The counters are incremented on the occurrence of a measured R—R intervals falling within associated rate ranges. These rate ranges may be defined by the programming stored in the RAM 526

The following exemplary VT/VF detection method corresponds to that employed in commercially marketed Medtronic implantable pacemaker/cardioverter/defibrillators and employs rate/interval based timing criteria as a basic mechanism for detecting the presence of a tachyarrhythmia. To this end, the device defines a set of rate ranges and associated software-defined counters to track the numbers of intervals falling within the defined ranges.

A first rate range may define a minimum R—R interval used for fibrillation detection, referred to as "FDI". The associated VF count preferably indicates how many of a first predetermined number of the preceding R—R intervals were less than FDI.

A second rate range may include R—R intervals less than a lower tachycardia interval "TDI", and the associated VT count (VTEC) is incremented in response to an R—R interval less than TDI but greater then FDI, is not affected by R—R intervals less than FDI, and is reset in response to R—R intervals greater than TDI.

Optionally, the device may include a third rate range including R—R intervals greater than the FDI interval, but less than a fast tachycardia interval (FTDI) which is intermediate the lower tachycardia interval (TDI) and the lower fibrillation interval (FDI).

For purposes of the present example, the counts may be used to signal detection of an associated arrhythmia (ventricular fibrillation, fast ventricular tachycardia or lower rate ventricular tachycardia) when they individually or in combination reach a predetermined value, referred to herein as "NID's" (number of intervals required for detection). Each rate zone may have its own defined count and NID, for example "VFNID" for fibrillation detection and "VTNID" for ventricular tachycardia detection or combined counts may be employed. These counts, along with other stored information reflective of the previous series of R— R intervals such as information regarding the rapidity of onset of the detected short R—R intervals, the stability of the detected R—R intervals, the duration of continued detection of short R—R intervals, the average R—R interval duration and information derived from analysis of stored EGM segments are used to determine whether tachyarrhythmia are present and to distinguish between different types of tachyarrhythmia. For purposes of illustrating the invention, an exemplary rate/interval based ventricular tachyarrhythmia detection method is described above. Other tachyarrhythmia detection methodologies, including detection methods as described in U.S. Pat. No. 5,991,656, issued to Olson, et al. on Nov. 23, 1999, U.S. Pat. No. 5,755,736, issued to Gillberg, et al. on May 26, 1998, both incorporated herein by reference in their entireties, or other known ventricular and/or atrial tachyarrhythmia detection methods may be substituted. It is believed that the discrimination methods of the present invention may be usefully practiced in conjunction with virtually any underlying atrial or ventricular tachyarrhythmia detection scheme. Other exemplary detection schemes are described in U.S. Pat. No. 4,726,380, issued to Vollmann, U.S. Pat. No. 4,880,005, issued to Pless et al., U.S. Pat. No. 4,830,006, issued to Haluska et al., and U.S. patent application Ser. No. 09/566,477, filed May 8, 2000 by Gillberg et al., all incorporated by reference in their entireties herein. An additional set of tachycardia recognition methodologies is disclosed in the article "Onset and Stability for Ventricular Tachyarrhythmia Detection in an Implantable Pacer-Cardioverter-Defibrillator" by Olson et al., published in *Computers in Cardiology*, Oct. 7–10, 1986, IEEE Computer Society Press, pages 167–170, also incorporated by reference in its entirety herein. However, other criteria may also be measured and employed in conjunction with the present invention.

Figure 3:
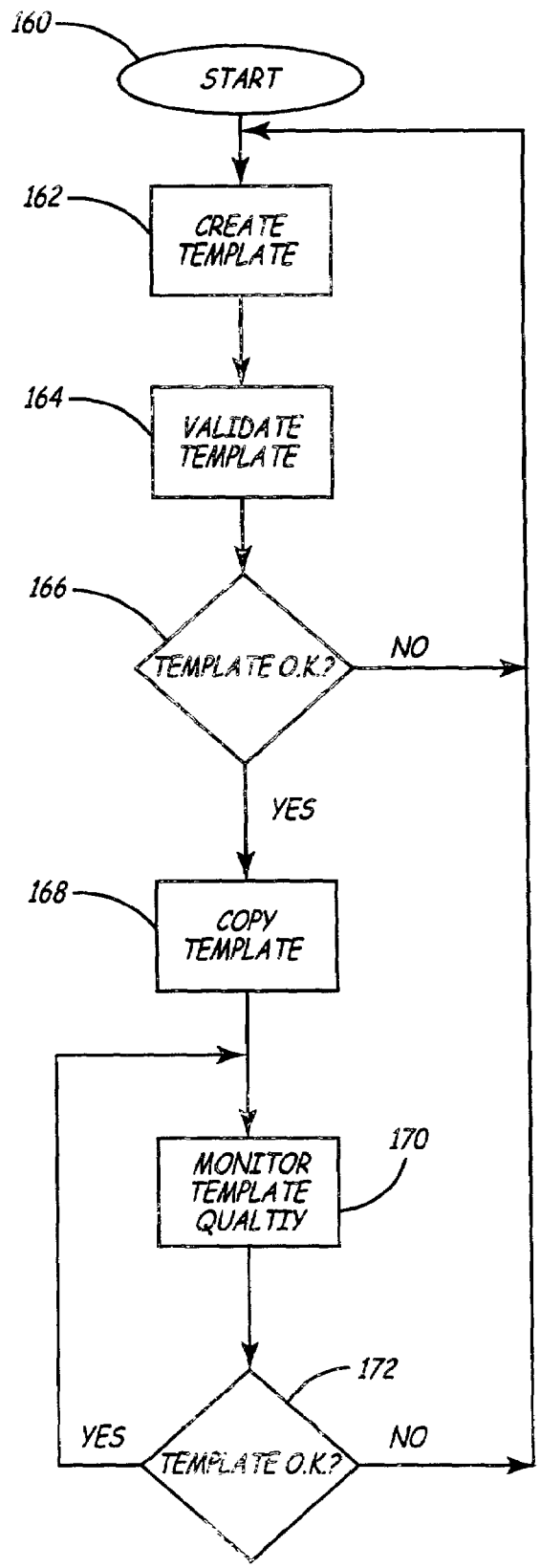
FIG. 3 is a flowchart of generation of a template for an implantable medical device according to the present invention.

FIG. 3 is a flowchart of generation of a template for an implantable medical device according to the present invention. As illustrated in FIGS. 2 and 3, generation of a supraventricular rhythm template according to the present invention is initiated by microprocessor 524, either automatically or manually at Step 160, using R-waves of the digitized EGM signals stored in random access memory 526. The generation of the template is initiated, for example, when no template currently exists, or upon recognition, either automatically by the implantable medical device, or manually by a physician, that the current template is no longer accurate, as will be described below. Once the automatic template generation process is initiated in Step 160, and a template is created, Step 162, a determination is then made as to whether the created template is valid, Steps 164 and 166. If it is determined that the template is not valid, No in Step 166, the template is discarded and the process returns to step 160 to create a new template. However, if it is determined that the template is valid, YES in Step 166, the template is copied in a permanent position for VT/SVT discrimination, Step 168. According to the present invention, once created, the quality of the valid template continues to be monitored, Step 170, and a determination is made in Step 172 as to whether the template continues to be a valid template, i.e., whether the template is an accurate representation of a supraventricular rhythm of the patient. If it is determined in Steps 170 and 172 that the template is no longer valid, No in Step 172, the process returns to step 160 to create a new template. Once the new template is created and validated in Steps 162–166, the new template is copied in the permanent position, Step 168, replacing the previous template, and the quality of the new template is monitored, Steps 170 and 172. On the other hand, if it is determined that the template is valid, i.e., that the template continues to be an accurate representation of a supraventricular rhythm of the patient, YES in Step 172, the device continues to monitor the template quality, Step 170, and so on.

Figure 3A:
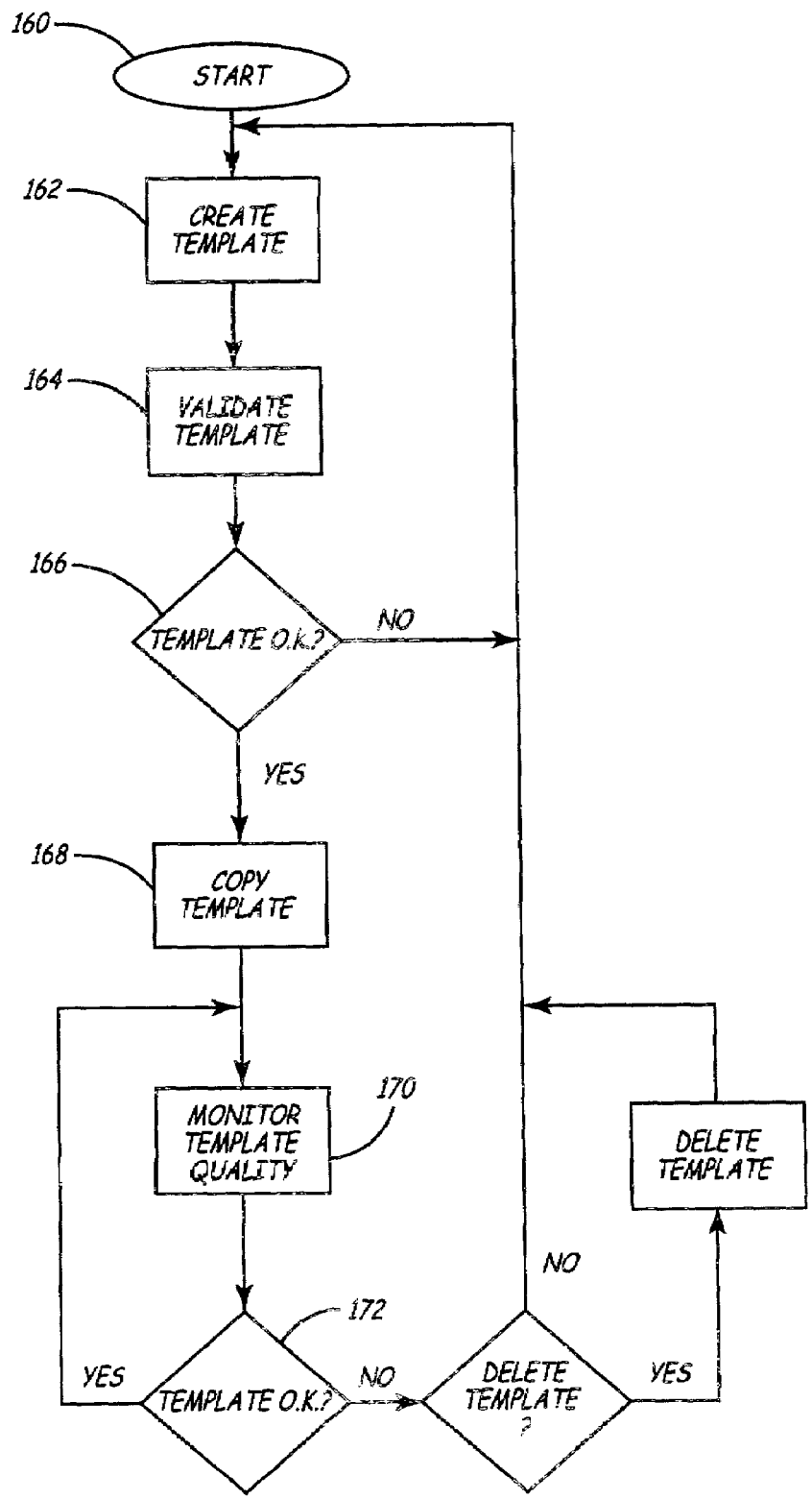
FIG. 3A is a flowchart of generation of a template for an implantable medical device according to an alternate embodiment of the present invention.

FIG. 3A is a flowchart of generation of a template for an implantable medical device according to an alternate embodiment of the present invention. As illustrated in FIG. 3A, an alternate embodiment of the present invention is similar to the template generation described above in reference to FIG. 3, and therefore description of Steps 160–172 is omitted merely for brevity sake. However, the alternate embodiment of FIG. 3A differs from the embodiment described above in reference to FIG. 3 in that once it is determined that the template is no longer valid in Steps 170 and 172, a determination is then made as to whether the template currently copied in the permanent position should be deleted, Step 173, based on the results of the monitored quality of the beats in Step 170, prior to returning to Step 160 to create a new template. If the results of the monitored quality beats is within a predetermined threshold, NO in Step 173, the process returns to Step 160 to create a new template. However, if the results of the monitored quality beats is not within the predetermined threshold, YES in Step 173, the template currently copied in the permanent position should is deleted, Step 175, and the process returns to Step 160 to create a new template.

Figure 4:
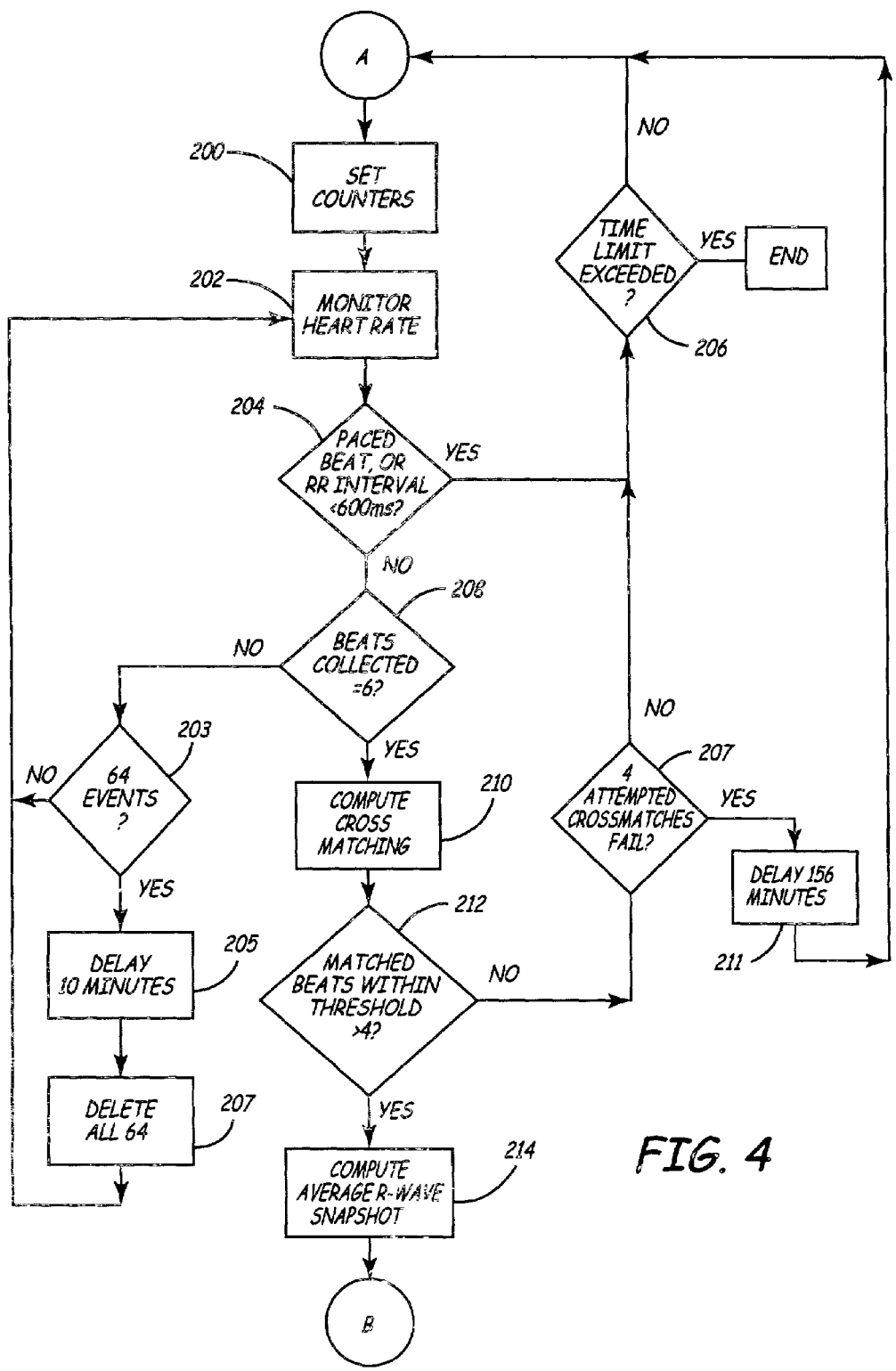
FIG. 4 is a flowchart of generation of a template for an implantable medical device according to the present invention.

FIG. 4 is a flowchart of generation of a template for an implantable medical device according to the present invention. As illustrated in FIGS. 2 and 4, a process for generation of a supraventricular rhythm template according to the present invention is initiated by microprocessor 524, either automatically or manually, using R-waves of the digitized EGM signals stored in random access memory 526 at regular intervals. The template generation process is initiated, for example, when no template currently exists, or upon recognition, either automatically by the implantable medical device, or manually by a physician, that the current template is no longer accurate, as will be described below. Upon initiation of the automatic template generation process, microprocessor 524 sets counters corresponding to the number of beats collected, the matched beats collected, and the average R-wave to zero, Step 200 and begins monitoring the heart rate of the patient, Step 202.

Microprocessor 524 next determines whether a beat is a normal beat by determining whether the beat is a paced beat, a beat immediately following a paced beat, or has an R—R interval less than 600 ms, Step 204. If the beat is determined to be a paced beat or to have an R_R interval below 600 ms in Step 204, and therefore not a normal beat, a determination is made as to whether a predetermined time period has been exceeded, Step 206, so that if the amount of time required to collect the number of normal beats required to create the template exceeds a predetermined threshold, the template generation process will be aborted and the VT/SVT discrimination algorithm utilizing EGM morphology may be set to PASSIVE mode (if there is a template already created within the device) or to OFF mode, and attempts to create a new template will be repeated after a predetermined time period has expired.

If the beat is determined to be a normal beat, i.e., the beat is neither a paced beat, a beat immediately following a paced beat, or has an R—R interval less than 600 ms, a determination is made as to whether a predetermined number of normal beats have been collected, Step 208. For example, according to a preferred embodiment of the present invention, a determination is made in Step 208 as to whether six beats have been collected. It is understood, however, that the number of beats chosen for the predetermined number of beats used in Step 208 is merely a matter of design choice that may be programmed within the device, and therefore the present invention is not intended to be limited to the use of six beats in Step 208.

If it is determined in Step 208 that the predetermined number of normal beats has not been collected, a determination is then made as to whether a predetermined number of events, i.e., paced beats, a beat immediately following a paced beat, beats having R—R intervals less than 600 ms, and normal beats, for example, have been collected, Step 203. For example, according to a preferred embodiment of the present invention, a determination is made in Step 203 as to whether 64 events have been collected, although it is understood that the present invention is not limited to the use of 64 events. If the predetermined number of events have not been collected, the process continues by examining the next beat, Step 202. On the other hand, if the predetermined number of normal beats have not been collected, NO in Step 208, and the predetermined number of events have been collected, YES in Step 203, microprocessor 524 determines that the predetermined number of normal beats, i.e., six for example, have not been obtained within a predetermined window, i.e., within 64 events. As a result, if the predetermined number of normal beats have not been collected within a predetermined number of collected events, microprocessor 524 delays further attempts at creating a template for a predetermined period of time, Step 205, delaying monitoring of the heart rate of the patient, and as a result, reducing current drain. For example, according to the present invention, current consumption is reduced by delaying generation of the template for approximately ten minutes, although it is understood that the predetermined delay is programmable and the present invention is not intended to be limited to a ten minute delay. Once the predetermined delay is completed, microprocessor 524 clears the predetermined number of collected events, i.e., the 64 events, Step 207, and once again begins monitoring the heart rate of the patient, Step 202.

In this way, according to the present invention, the process of generating the template continues until the predetermined number six normal beats have been collected, but is delayed for a predetermined period of time if the predetermined number of normal beats is not received within the predetermined number of collected events. Once the six normal beats are collected within the predetermined window, microprocessor 524 computes cross matches between the collected normal beats, Step 210. For example, according to the present invention, the first beat is matched against the second through sixth beats to generate five cross matches. A determination is then made as to whether four or more of the computed cross matches are similar within a predetermined threshold, Step 212. For example, according to a preferred embodiment of the present invention, the predetermined threshold of Step 212 is nominally 70%, although any value could be chosen without deviating from the present invention.

If four or more of the computed cross matches are not similar within the predetermined threshold, a determination is made as to whether a predetermined time period, such as one hour for example, or a predetermined number of attempts, such as three for example, has been exceeded, Step 206, so that if the amount of time required to collect the number of cross matches required to create the template exceeds a predetermined threshold, the template generation process will be aborted and attempts to create a new template will be repeated after a predetermined time period has expired. In particular, according to a preferred embodiment of the present invention, each time it is determined in Step 212 that four or more of the of the computed cross matches are not similar within the predetermined threshold, a determination is made as to whether a predetermined number of attempts at cross matching have failed to provided the number of similar computed cross matches required in Step 212, and if so, the process is delayed for a predetermined time period, resulting in reduced current drain on the device 100. For example, according to a preferred embodiment of the present invention, if it is determined in Step 206 that the cross matching threshold has not been reached within four attempts, the process is delayed for approximately 156 minutes, although the present invention is not intended to be limited to four failed cross matching attempts or to a delay of 156 minutes, but is intended to include any number of failed cross matching attempts and/time period that would be considered to be appropriate. However, if it is determined in Step 212 that four or more of the computed cross matches are similar within the predetermined threshold, the four or more cross matches that are similar within the predetermined threshold are averaged to create an average R wave snapshot, Step 214, that is then used as the template.

Figure 5:
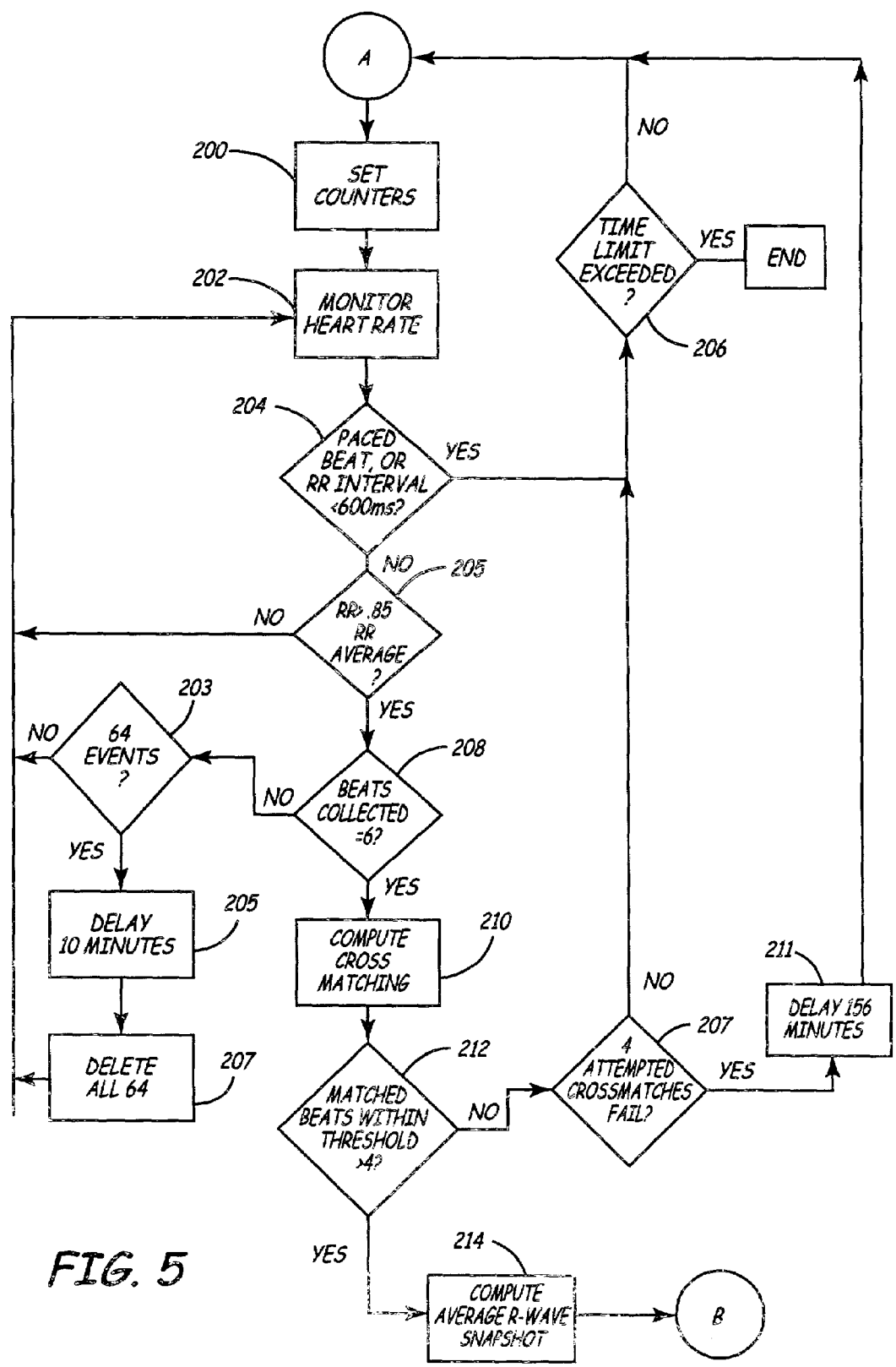
FIG. 5 is a flowchart of generation of a template for an implantable medical device according to an alternate preferred embodiment of the present invention.

FIG. 5 is a flowchart of generation of a template for an implantable medical device according to an alternate preferred embodiment of the present invention. According to an alternate embodiment of the present invention, the automatic template generation process is similar to the process described above in reference to FIG. 4, although an additional step is included in the alternate embodiment to exclude premature ventricular contractions. In particular, as illustrated in FIG. 5, if the beat is determined to be a normal beat, i.e., the beat is neither a paced beat, a beat immediately following a paced beat, or has an R—R interval less than 600 ms in Step 204, a determination is made as to whether the R—R interval is greater than a predetermined average R—R interval, Step 205. In particular, according to a preferred embodiment of the present invention, a determination is made as to whether the R—R interval is greater than approximately 85% of the average R—R interval. However, it is understood that any percentage value could be chosen as long as the chosen percentage value serves to exclude premature ventricular contractions.

If it is determined in Step 205 that the R—R interval is not greater than 85% of the average R—R interval, i.e., the likelihood that the beat is representative of a premature ventricular contraction is great, the beat is excluded, and the process returns to Step 202 to monitor a next beat. On the other hand, if it is determined that the R—R interval is greater than 85% of the average interval, i.e., it is not likely that the beat is representative of a premature ventricular contraction, the process continues at Step 208 as described above in FIG. 4. Since the steps illustrated in FIG. 5, with the exception of Step 205, have previously been described above in reference to FIG. 4, description of the steps other than Step 205 has not been repeated merely for the sake of brevity.

While the present invention is described above as computing cross matches between beats once six beats have been collected, and determining whether four of the cross matches exceed the threshold, it is understood that the present invention is not limited to the use of six beats and four cross matches, but rather any number of beats and cross matches could be utilized, depending upon the particular patient or device requirements involved.

Figure 6:
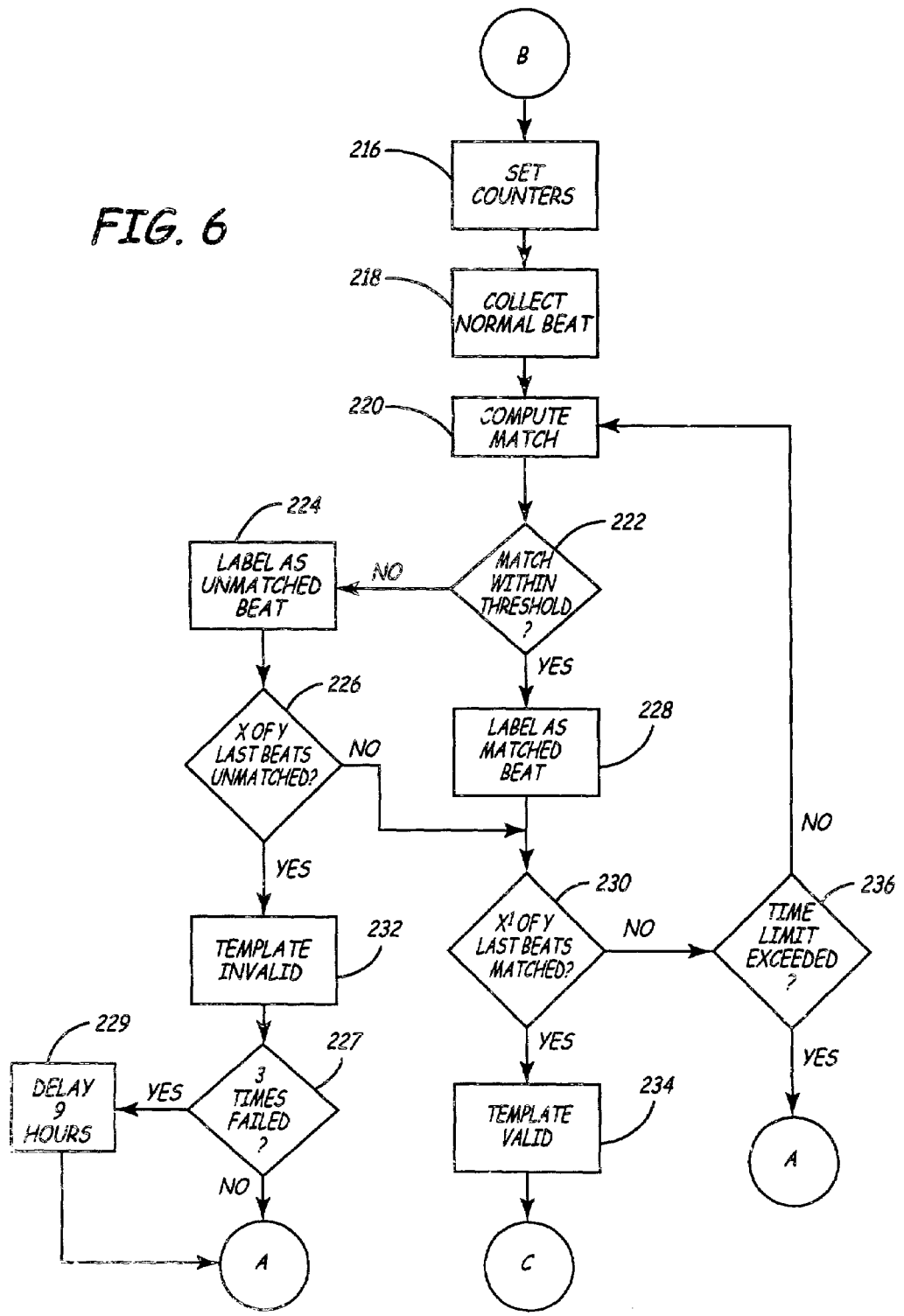
FIG. 6 is a flowchart of statistical validation of a template for an implantable medical device according to an alternate preferred embodiment of the present invention.

FIG. 6 is a flowchart of statistical validation of a template for an implantable medical device according to the present invention. According to the present invention, once the average R wave is created in the template generation stage described above for use as the template, the quality of the template is evaluated, based on matches between the template and ongoing slow heart rhythm, which according to a preferred embodiment of the present invention, is chosen as being slower than 100 bpm. It is understood that any rate could be chosen as the slow heart rhythm for the statistical validation or creation of the template, and therefore the invention is not limited to rates slower than 100 bpm.

As illustrated in FIGS. 2 and 6, once the template has been generated, microprocessor 524 sets counters corresponding to the total beat number, the number of matched beats, and the number of bad beats to zero, Step 216. Microprocessor then collects one normal beat from every N beats, where N is equal to one hundred, Step 218, and computes a match between the collected beat and the template, Step 220. According to an alternate embodiment of the present invention, in order to reduce current drain, microprocessor 524 collects one beat within a predetermined time period, such as one beat every ten seconds, for example.

A determination is then made as to whether the collected beat matches the template within a predetermined threshold, Step 222. For example, according to the present invention, a determination is made as to whether the collected beat matches are nominally within approximately 70% of a predetermined threshold. However, the threshold is not limited to this value, and could be programmed as determined by a physician. If the collected beat does not match the template within the threshold, the beat is labeled as an unmatched beat, Step 224 and a determination is made as to whether x out of the last y number of beats nave been labeled as unmatched beats, Step 226. If x out of the last y number of beats are unmatched beats, YES in Step 226, the template is determined to be invalid, Step 232. According to the present invention, once the template has been determined to be invalid in Step 232, a determination is made as to whether a predetermined number of attempts at statistically validating the template have failed, Step 227. If the predetermined number of attempts at statistically validating the template have been unsuccessful so that statistical validation has failed the predetermined number of times, YES in Step 227, the statistical validation process is delayed for a predetermined period of time, Step 229, thereby reducing current drain on the device 100. Once the statistical validation process has been delayed for the predetermined time period, the template generation process is repeated.

In particular, according to a preferred embodiment of the present invention, if it is determined in Step 227 that three attempts at statistically validating the template have failed, the process is delayed for approximately nine hours, although it is understood that the present invention is not intended to be limited to three attempts in Step 227 or to nine hours in Step 229, but would include any number of attempts and/or period of delay. On the other hand, if it is determined in Step 227 that there have not been the predetermined number of failed attempts at statistically validating the template, NO in Step 227, the template generation process is repeated, i.e., the process returns to portion A of FIG. 4 or FIG. 5.

On the other hand, if the collected beat does match the template within the threshold, YES in Step 222, the beat is labeled as a matched beat, Step 228. Once the beat is labeled as a matched beat, Step 228, or it is determined that x out of the last y number of beats are not unmatched beats in Step 226, a determination is made as to whether x' out of the last y number of beats are matched beats, Step 230. If x' out of the last y number of beats are not matched beats, a determination as made as to whether a predetermined time period has been exceeded, Step 236, so that if attempts to statistically validate the template are not successful within the predetermined time period of Step 236, the template generation process is repeated, i.e., the process returns to portion A of FIG. 4 or FIG. 5.

However, if it is determined in Step 236 that the predetermined time period has not been exceeded, microprocessor 524 collects another beat and the process is repeated, Step 218. In this way, the statistical validation portion is continued until x' number of beats are determined to be matched beats or until x number of beats are determined to be unmatched beats, whichever occurs first, either within y number of beats or within the time limit. Once x' out of y number of beats are determined to be within the threshold, the template is accepted as valid, Step 234, and is then copied into the location where the template is used by microprocessor 524 to perform the morphology discrimination. However, if x out of y number of beats are determined to not be within the threshold prior to determining that x' out of y number of beats are within the threshold at Step 222, the process returns to Step A and a new template is generated.

According to a preferred embodiment of the present invention, the x number of beats is equal to thirty, the x' number of beats is equal to seventy, and the y number of beats is equal to one hundred, so that a determination is made in Step 226 as to whether thirty out of the last one hundred collected beats are unmatched beats and 230 as to whether seventy out of the last one hundred collected beats are matched beats in Step 230 of FIG. 6. However, it is understood that, according to the present invention, the values for x, x', and y is not limited to thirty, seventy, and one hundred, respectively. Rather, the present invention is intended to include the use of any number of beats of last collected beats to monitor the quality of the template and determine whether the template is valid.

Figure 7:
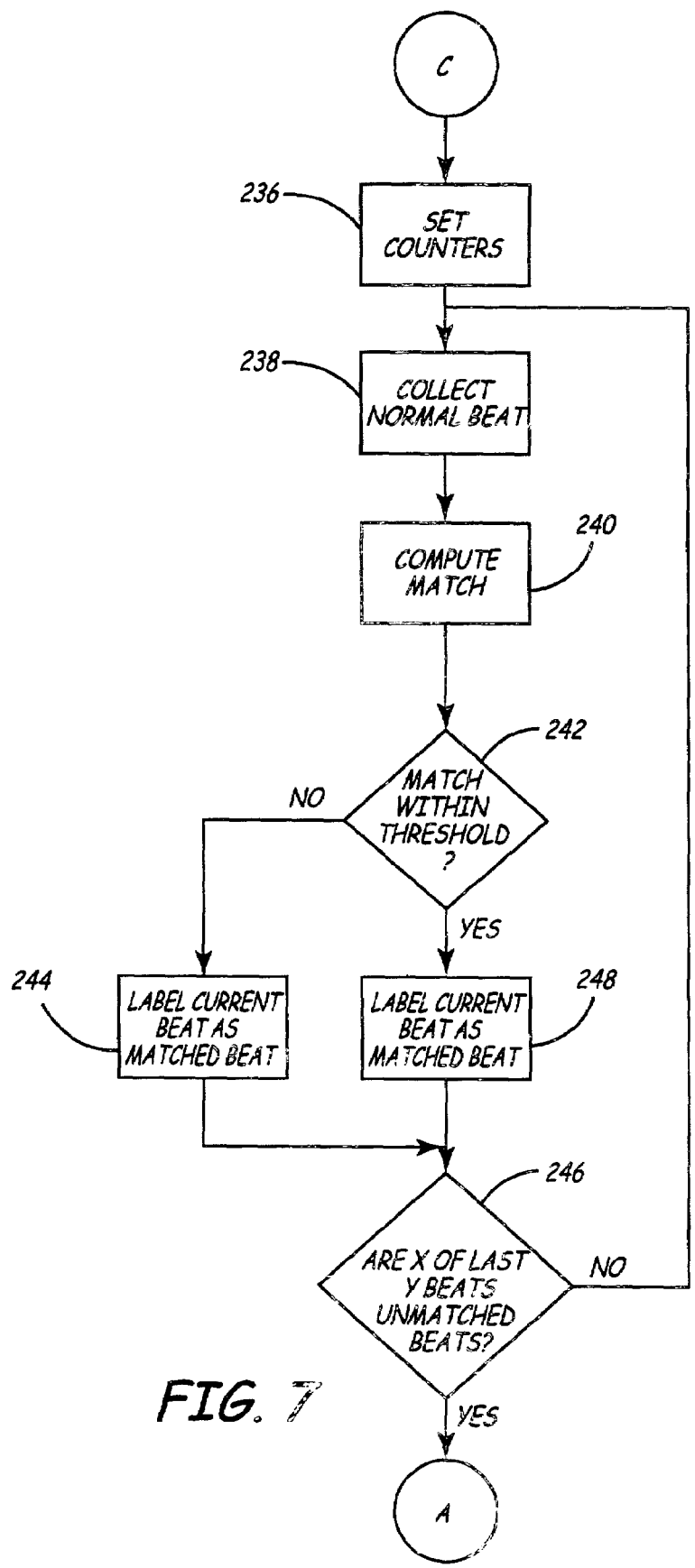
FIG. 7 is a flowchart of monitoring of template quality for an implantable medical device according to the present invention.

FIG. 7 is a flowchart of monitoring of template quality for an implantable medical device according to the present invention. As illustrated in FIGS. 2 and 7, once microprocessor 524 determines that the template is validated (Step C in FIG. 6), microprocessor 524 sets counters corresponding to the total number of beats, the number of evaluated beats, the number of matched beats, and the number of bad beats to zero, Step 236. Microprocessor 524 then collects one normal beat from every N beats, where N is equal to one thousand, Step 238, and computes a match between the beat and the template, Step 240. According to an alternative embodiment of the present invention, microprocessor 524 collects one normal beat within a predetermined time period, for example one normal beat is collected approximately every one thousand seconds.

Once the match between the beat and the template is computed, microprocessor 524 determines whether the collected beat matches the template within a predetermined threshold, Step 242. If the collected beat does not match the template within the threshold, the beat is labeled as a bad, or unmatched beat, Step 244 and a determination is made as to whether x out of the last y number of beats are unmatched beats, Step 246. If x out of the last y number of beats are unmatched beats, the template is determined to be invalid, and the template generation process is repeated, i.e., the process returns to portion A of FIG. 4. On the other hand, if x of the last y number of beats are not unmatched beats in Step 246, another normal, regular beat from one thousand beats is collected, Step 238 and the process is repeated.

If the collected beat does match the template within the threshold, YES in Step 242, the beat is labeled as a good, or matched beat, Step 248, and the determination is made at Step 246 as to whether x of the last y number of beats are unmatched beats. If x out of the last y number of beats are unmatched beats, the template is determined to be invalid, and the template generation process is repeated, i.e., the process returns to portion A of FIG. 4. On the other hand, if x of the last y number of beats are not unmatched beats in Step 246, another regular beat from one thousand beats is collected, Step 238 and the process is repeated.

According to a preferred embodiment of the present invention, the x number of beats is equal to thirty and the y number of beats is equal to one hundred, so that a determination is made in Step 246 as to whether thirty out of the last one hundred collected beats are unmatched beats. However, it is understood that, according to the present invention, the values for x and y is not limited to thirty and one hundred, respectively. Rather, the present invention is intended to include the use of any number of beats of last collected beats to monitor the quality of the template and determine whether the template is valid.

In this way, the monitoring stage of the present invention, illustrated in FIG. 6, is similar to the statistical validation of the template stage, illustrated in FIG. 7, with the exception that one out of every one thousand beats are evaluated and once more than thirty out of the last one hundred beats do not match the template within the threshold, an attempt is made to create a new template, Step A of FIG. 4. In addition, the monitoring stage is continuous unless x out of the last y beats are determined to be unmatched beats in Step 246, i.e., the template is invalid, in which case the process returns to portion A of FIG. 4 to re-generate the template. While the characteristic time for the monitoring stage of FIG. 7 is approximately 20–30 hours, if there is a change in the EGM morphology, the change will be picked up by the present invention in approximately one-third of this characteristic time (i.e., 7–10 hours), since it only takes 30 mismatches to reject the template.

Figure 8:
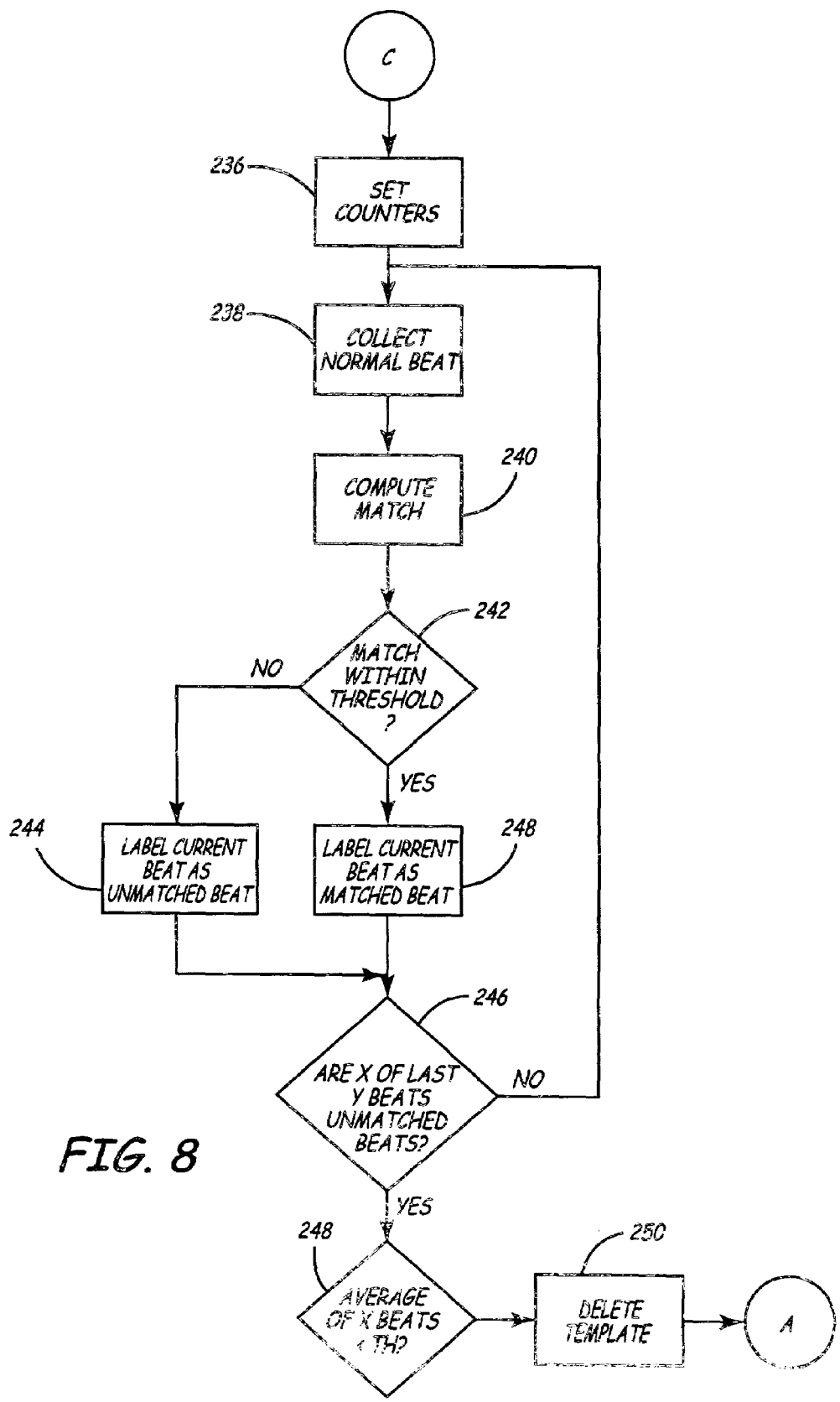
FIG. 8 is a flowchart of monitoring of template quality for an implantable medical device according to an alternate embodiment of the present invention.

FIG. 8 is a flowchart of monitoring of template quality for an implantable medical device according to an alternate embodiment of the present invention. As illustrated in FIG. 8, an alternate embodiment of the template monitoring process according to the present invention is similar to the template monitoring process described above in reference to FIG. 7, and therefore description of Steps 236–246 of FIG. 8 is omitted merely for brevity sake. However, the alternate embodiment of FIG. 8 differs from the embodiment described above in reference to FIG. 7 in that if x out of the last y number of beats are determined to be unmatched beats in Step 246, a determination is then made as to whether an average degree of similarity between the unmatched beats (x in step 246) and the template is less than a predetermined threshold, Step 248, such as a fraction of the threshold used to label beats as matched or unmatched in Step 242. If the average degree of similarity between the unmatched beats and the template is less than the predetermined threshold, YES in Step 248, the template currently copied in the permanent position is deleted, Step 250, the process returns to Step 160 to create a new template. On the other hand, if the average degree of similarity between the unmatched beats and the template is greater than or equal to the predetermined threshold, NO in Step 248, the template currently copied in the permanent position is not deleted and the process returns to Step 160 to create a new template.

According to a preferred embodiment of the present invention, the threshold used in Step 248 is selected as 50% of the threshold utilized in Step 242, although it is understood that any threshold could be utilized in accordance with the present invention that identifies the necessity to delete the current template prior to attempting to create a new template.

It is understood that while the present invention has been described above as validating a template once seventy matched beats have been collected and invalidating the template once thirty collected beats do not match the template within a threshold, the present invention is not intended to be limited to requiring seventy out of one hundred beats to match the template within the threshold in order for the template to be determined to be statistically valid. Rather, any number of beats could be utilized in the statistical evaluation. Similarly, while the present invention has been described above as monitoring the quality of the template once seventy matched beats have been collected out of one hundred beats over a total of one thousand beats, and invalidating the template once thirty out of the last one hundred collected beats do not match the template within a threshold, any number of beats could be utilized in the monitoring of the quality of the template.

It is further understood that while the present invention has been described in terms of its application to a single chamber system in FIG. 1, the present invention is not intended to be limited to such single chamber systems, but rather can be utilized in other systems, such as the dual chamber system described, for example, in U.S. Pat. No. 6,141,581 issued to Olson et al, on Oct. 31, 2000, incorporated herein by reference in its entirety.

It is understood that according to the present invention, a "normal" beat is described as a beat that is not a paced beat, not a beat immediately following a paced beat, not a beat with an R—R interval less than a predetermined maximum rate (i.e., 600 ms or VT detection interval (TDI)+60), and optionally as a beat that is not associated with a premature ventricular contraction, i.e., a beat having an R—R interval greater than a certain percentage of an average R—R interval, such as 0.85 R—R for example.

In addition, the present invention includes a set of criteria for interrupting or further delaying the template creation, validation and quality monitoring (steps 162, 164, and 170 in FIG. 3) during a time period when the intracardiac EGM signal may be unstable due to recent anti-tachycardia therapy or tachyarrhythmia events.

For example, according to the present invention, if a tachycardia episode (including VT monitor episode) occurs, or if a clinician initiates a device programming change that may effect the EGM signal (for example, delivery of tachyarrhythmia therapy, induction of a tachyarrhythmia event) any of the template processes will be stopped for a programmable period of time, such as 1 hour for example. If the template creation process was ongoing, the collected samples (FIG. 208 in FIG. 4) will be cleared and the template creation process will start over (A in FIG. 4) after the programmable period of time expires. Template validation and template creation processes will be suspended (counters are not cleared) for the programmable duration. If the clinician initiates a device programming changes that changes the EGM signal characteristics (e.g. signal vector, signal gain, signal filtering), the current template will be deleted. Once the current template is deleted after a physician initiated EGM signal change, the template creation process will be restarted with or without a delay of a programmable period of time.

Finally, it is understood that while the beats that are collected in Step 238 of FIG. 7 and Step 218 of FIG. 6, are described as being one out of one thousand and one out of one hundred, respectively, the present invention is not intended to be limited to those counts, but rather may utilize any number of counts, dependent upon physician and/or system requirements.

The preceding specific embodiments are illustrative of the practice of the invention. It is to be understood, therefore, that other expedients known to those of skill in the art or disclosed herein may be employed. In the following claims, means-plus-function clauses are intended to cover the structures described herein as performing the recited function and not only structural equivalents but also equivalent structures. For example, although a nail and a screw may not be structural equivalents in that a nail employs a cylindrical surface to secure wooden parts together, whereas a screw employs a helical surface, in the environment of fastening wooden parts, a nail and a screw are equivalent structures. It is therefore to be understood, that within the scope of the appended claims, the invention may be practiced otherwise than as specifically described without actually departing from the spirit and scope of the present invention.

What is claimed is:

1. A method of generating a template in an implantable medical device for implantation within a patient, comprising the steps of:

generating a template from collected events corresponding to the patient;

delaying the step of generating a template for a first predetermined time period in response to the template not being generated within a predetermined number of collected events;

determining whether the template is valid; and monitoring the template to determine whether the template is an accurate representation of the patient, wherein the step of generating a template comprises the steps of:

monitoring a heart rate of the patient to generate the collected events;

determining whether beats corresponding to the collected events are normal beats; and determining whether a predetermined number of normal beats has been collected within the predetermined number of collected events, wherein the step of delaying the template generation includes delaying the template generation in response to the predetermined number of normal beats not being collected within the predetermined number of collected events, and wherein the step of generating a template further comprises:

determining whether the predetermined number of normal beats have been collected and computing cross matches between the predetermined number of collected normal beats to form corresponding computed cross matches;

determining whether a predetermined number of the computed cross matches exceed a threshold;

determining whether a predetermined number of cross matching attempts have failed;

delaying the template generation for a second predetermined time period in response to the predetermined number of failed cross matching attempts; and forming the template from the predetermined number of computed cross matches in response to the predetermined number of the computed cross matches exceeding the threshold.

2. The method of claim 1, wherein the predetermined number of cross matches is four and the second predetermined time period is approximately equal to 156 minutes.

3. The method of claim 1, wherein the predetermined number of beats is six and the predetermined number of computed cross matches is four.

4. The method of claim 1, wherein the step of monitoring the template comprises the steps of:

(a) collecting subsequent normal beats within a second predetermined time period;

(b) computing a match between a subsequently collected beat and the template;

(c) determining whether the match is within a predetermined threshold to form matched beats and other than matched beats;

(d) determining whether x out of the last y subsequently collected beats are other than matched beats; and (e) repeating steps (a)–(d) in response to x out of the last y beats not being other than matched beats.

5. The method of claim 4, wherein step (a) comprises collecting one normal beat every 1000 seconds.

6. The method of claim 4, wherein the step of computing a match comprises computing the match for one out of every one thousand subsequently collected beats and the template.

7. The method of claim 4, further comprising the step of repeating the step of generating a template in response to x out of the last y beats being other than matched beats.

8. A method of generating a template in an implantable medical device for implantation within a patient, comprising the steps of:

generating a template from collected events corresponding to the patient;

delaying the step of generating a template for a first predetermined time period in response to the template not being generated within a predetermined number of collected events;

determining whether the template is valid; and monitoring the template to determine whether the template is an accurate representation of the patient wherein the step of determining whether the template is valid comprises the steps of:

collecting subsequent normal beats within a second predetermined time period;
computing a match between the subsequently collected normal beats and the template;
determining whether the match is within a predetermined threshold to form matched beats and other than matched beats;
determining whether the other than matched beats is greater than a first number of beats; and
determining the template is valid in response to the matched beats being greater than or equal to a second number of beats, wherein, in response to the other than matched beats being greater than the first number of beats, the step of determining whether the template is valid further comprises the step of:
determining whether attempts to validate the template have failed a predetermined number of times;
repeating the step of generating a template in response to validation of the template not having failed the predetermined number of times; and
delaying the step of determining whether the template is valid for a third predetermined time period in response to validation of the template having failed the predetermined number of times.

9. The method of claim 8, wherein the step of collecting subsequent normal beats comprises collecting one normal beat within 10 seconds.

10. The method of claim 8, wherein the third predetermined time period is approximately equal to 9 hours and the predetermined number of times is three.

11. The method of claim 8, wherein the first number of beats is thirty and the second number of beats is seventy.

12. The method of claim 8, further comprising, in response to the matched beats not being greater than or equal to the second number of beats, the steps of:
determining whether a match has been computed for a predetermined number of beats;
determining whether a time period has been exceeded in response to the match not being computed for the predetermined number of beats; and
repeating the step of generating a template in response to the predetermined time period being exceeded.

13. The method of claim 12, wherein the first number of beats is thirty, the second number of beats is seventy, and the predetermined number of beats is one hundred.

14. A method of generating a template in an implantable medical device for implantation within a patient, comprising the steps of:
generating a template from collected events corresponding to the patient;
delaying the step of generating a template for a first predetermined time period in response to the template not being generated within a predetermined number of collected events;
determining whether the template is valid; and
monitoring the template to determine whether the template is an accurate representation of the patient, wherein the step of monitoring the template comprises the steps of:
(a) collecting subsequent normal beats within a second predetermined time period;
(b) computing a match between a subsequently collected beat and the template;
(c) determining whether the match is within a predetermined threshold to form matched beats and other than matched beats;
(d) determining whether x out of the last y subsequently collected beats are other than matched beats; and
(e) repeating steps (a)–(d) in response to x out of the last y beats not being other than matched beats, the method further comprising, in response to x out of the last y beats being other than matched beats, the steps of:
determining whether an average degree of similarity between the other than matched beats and the template is less than a predetermined threshold;
deleting the template in response to the average degree of similarity between the other than matched beats and the template being less than the predetermined threshold; and
generating a template in response to the average degree of similarity between the other than matched beats and the template being greater than or equal to the predetermined threshold.

15. A method of generating a template in an implantable medical device for implantation within a patient, comprising the steps of:
generating a template from collected events corresponding to the patient;
delaying the step of generating a template for a first predetermined time period in response to the template not being generated within a predetermined number of collected events;
determining whether the template is valid; and
monitoring the template to determine whether the template is an accurate representation of the patient, wherein the step of monitoring the template comprises the steps of:
(a) collecting subsequent normal beats within a second predetermined time period;
(b) computing a match between a subsequently collected beat and the template;
(c) determining whether the match is within a predetermined threshold to form matched beats and other than matched beats;
(d) determining whether x out of the last y subsequently collected beats are other than matched beats; and
(a) repealing steps (a)–(d) in response to x out of the last y beats not being other than matched beats, wherein x is thirty and y is one hundred.

16. A processor readable medium in an implantable medical device, comprising:
means for collecting events corresponding to the patient; and
means for generating a template corresponding from the collected events, the means for generating a template further delaying the template generation for a first predetermined time period in response to the template not being generated within a predetermined number of the collected events, determining whether the template is valid and monitoring the template to determine whether the template is an accurate representation of the supraventricular rhythm, wherein the generating means determines whether a predetermined number of normal beats have been collected and computes cross matches between the predetermined number of collected normal beats to form corresponding computed cross matches, determines whether a predetermined number of the computed cross matches exceed a threshold, determines whether a predetermined number of cross matching attempts have failed, delays the template generation for a second predetermined time period in response to the predetermined number of failed cross matching attempts, and forms the template from the predetermined number of computed cross matches in response to the predetermined number of the computed cross matches exceeding the threshold.

17. A processor readable medium in an implantable medical device, comprising;
means for collecting events corresponding to the patient; and
means for generating a template corresponding from the collected events, the means for generating a template further delaying the template generation for a first predetermined time period in response to the template not being generated within a predetermined number of the collected events, determining whether the template is valid and monitoring the template to determine whether the template is an accurate representation of the supraventricular rhythm, wherein the generating means determines whether attempts to validate the template have failed a predetermined number of times, generates a new a template in response to validation of the template not having failed the predetermined number of times, and delays determination of whether the template is valid for a second predetermined time period in response to validation of the template having failed the predetermined number of times.

18. A processor readable medium in an implantable medical device, comprising:
means for collecting events corresponding to the patient; and
means for generating a template corresponding from the collected events, the means for generating a template further delaying the template generation for a first predetermined time period in response to the template not being generated within a predetermined number of the collected events, determining whether the template is valid and monitoring the template to determine whether the template is an accurate representation of the supraventricular rhythm, wherein the generating means determines whether an average degree of similarity between the other than matched beats and the template is less than a predetermined threshold, deletes the template in response to the average degree of similarity between the other than matched beats and the template being less than the predetermined threshold, and generates a template in response to the average degree of similarity between the other than matched beats and the template being greater than or equal to the predetermined threshold.

19. An implantable medical device, comprising:
means for collecting events corresponding to a patient;
means for generating a template corresponding from the collected events;
means for delaying the template generation for a first predetermined time period in response to the template not being generated within a predetermined number of the collected events;
means for determining whether the template is valid and monitoring the template to determine whether the template is an accurate representation of the supraventricular rhythm;
means for determining whether a predetermined number of normal beats have been collected and computing cross matches between the predetermined number of collected normal beats to form corresponding computed cross matches;
means for determining whether a predetermined number of the computed cross matches exceed a threshold;
means for determining whether a predetermined number of cross matching attempts have failed;
means for delaying the template generation for a second predetermined time period in response to the predetermined number of failed cross matching attempts; and
means for generating the template from the predetermined number of computed cross matches in response to the predetermined number of the computed cross matches exceeding the threshold.

20. An implantable medical device, comprising:
means for collecting events corresponding to a patient;
means for generating a template corresponding from the collected events;
means for delaying the template generation for a first predetermined time period in response to the template not being generated within a predetermined number of the collected events;
means for determining whether the template is valid and monitoring the template to determine whether the template is an accurate representation of the supraventricular rhythm;
means for determining whether attempts to validate the template have failed a predetermined number of times and generating a new a template in response to validation of the template not having failed the predetermined number of times; and
means for delaying determination of whether the template is valid for a second predetermined time period in response to validation of the template having failed the predetermined number of times.

21. An implantable medical device, comprising:
means for collecting events corresponding to a patient;
means for generating a template corresponding from the collected events;
means for delaying the template generation for a first predetermined time period in response to the template not being generated within a predetermined number of the collected events;
means for determining whether the template is valid and monitoring the template to determine whether the template is an accurate representation of the supraventricular rhythm; and
means for determining whether an average degree of similarity between the other than matched beats and the template is less than a predetermined threshold, wherein the means for generating a template deletes the template in response to the average degree of similarity between the other than matched beats and the template being less than the predetermined threshold, and generates the template in response to the average degree of similarity between the other than matched beats and the template being greater than or equal to the predetermined threshold.

* * * * *

UNITED STATES PATENT AND TRADEMARK OFFICE
CERTIFICATE OF CORRECTION

PATENT NO. : 7,062,315 B2  Page 1 of 1
APPLICATION NO. : 10/132773
DATED : June 13, 2006
INVENTOR(S) : Lev A. Koyrakh et al.

It is certified that error appears in the above-identified patent and that said Letters Patent is hereby corrected as shown below:

Col. 20, line 41, please delete "(a) repealing" and insert --(e) repeating--.

Signed and Sealed this

Nineteenth Day of December, 2006

JON W. DUDAS
*Director of the United States Patent and Trademark Office*